US006792939B1

(12) United States Patent
Weinstein

(10) Patent No.: US 6,792,939 B1
(45) **Date of Patent: *Sep. 21, 2004**

(54) METHOD AND DEVICE FOR ORGANIZING AND COORDINATING THE COMBINED USE OF LIQUID MEDICATIONS FOR CONTINUOUS NEBULIZATION FOR THE TREATMENT OF RESPIRATORY DISORDERS

(76) Inventor: Robert E. Weinstein, 177 Commonwealth Ave., Boston, MA (US) 02116

( * ) Notice: Subject to any disclaimer, the term of this patent is extended or adjusted under 35 U.S.C. 154(b) by 0 days.

This patent is subject to a terminal disclaimer.

(21) Appl. No.: 10/448,510

(22) Filed: May 30, 2003

Related U.S. Application Data

(63) Continuation-in-part of application No. 09/908,176, filed on Jul. 19, 2001, now Pat. No. 6,571,790, which is a continuation-in-part of application No. 09/325,486, filed on Jun. 3, 1999, now abandoned, which is a continuation-in-part of application No. 08/855,893, filed on May 12, 1997, now Pat. No. 5,941,241.

(51) Int. Cl.[7] ........................ A61M 11/00; B65D 83/04

(52) U.S. Cl. ........................... 128/200.19; 128/200.14; 206/534; 206/538

(58) Field of Search ....................... 128/200.14, 200.19, 128/200.23, 203.12, 205.21, 205.23; 206/528, 534, 530, 538, 539, 532, 562, 563, 564, 828

(56) References Cited

U.S. PATENT DOCUMENTS

| | | | | | |
|---|---|---|---|---|---|
| 191,607 | A | | 6/1877 | Millard | |
| 2,110,572 | A | | 3/1938 | Foote | |
| 2,644,259 | A | | 7/1953 | Beadle | |
| 3,356,244 | A | * | 12/1967 | Witchell | 215/49 |
| 3,777,949 | A | * | 12/1973 | Chiquiari-Arias | 222/541.8 |
| 3,993,223 | A | * | 11/1976 | Welker et al. | 222/107 |
| 4,358,028 | A | * | 11/1982 | Chiquiar-Arias | 222/107 |
| 4,534,343 | A | | 8/1985 | Nowacki et al. | |
| 4,809,692 | A | | 3/1989 | Nowacki et al. | |
| 4,832,015 | A | | 5/1989 | Nowacki et al. | |
| 4,889,238 | A | | 12/1989 | Batchelor | |
| 4,890,741 | A | | 1/1990 | Edelstein | |
| 5,042,467 | A | | 8/1991 | Foley | |
| 5,076,474 | A | * | 12/1991 | Hansen | 222/420 |
| 5,215,079 | A | | 6/1993 | Fine et al. | |
| 5,261,571 | A | * | 11/1993 | Goncalves | 222/214 |
| 5,363,842 | A | | 11/1994 | Mishelevich et al. | |
| RE35,445 | E | | 2/1997 | Pora | |
| 5,664,557 | A | | 9/1997 | Makiej, Jr. | |
| 5,724,986 | A | | 3/1998 | Jones, Jr. et al. | |
| 5,830,490 | A | | 11/1998 | Weinstein et al. | |
| 5,839,430 | A | | 11/1998 | Cama | |
| 5,941,241 | A | | 8/1999 | Weinstein et al. | |
| 6,024,221 | A | | 2/2000 | Yuyana et al. | |
| 6,077,530 | A | | 6/2000 | Weinstein et al. | |
| 6,382,205 | B1 | * | 5/2002 | Weinstein et al. | 128/200.23 |
| 6,571,790 | B1 | * | 6/2003 | Weinstein | 128/200.19 |

* cited by examiner

*Primary Examiner*—Henry Bennett
*Assistant Examiner*—Teena Mitchell
(74) *Attorney, Agent, or Firm*—Altman & Martin

(57) ABSTRACT

A device and method for simplifying, organizing, and reducing medication error, and enhancing therapeutic compliance with the combined use of liquid medications for continuous nebulization for treating respiratory disorders comprising at least two separate liquids for continuously nebulized delivery to the respiratory tract, indicia for distinguishing the liquids, instructions for coordination of the liquids use together, a unifying container, and optionally, a spirometer. The method comprises providing the liquids, indicia, and instructions in the unified container, dispensing the prescribed amount of the liquids into the nebulization device, and administering the liquids according to the instructions.

7 Claims, 5 Drawing Sheets

METHOD AND DEVICE FOR ORGANIZING AND COORDINATING THE COMBINED USE OF LIQUID MEDICATIONS FOR CONTINUOUS NEBULIZATION FOR THE TREATMENT OF RESPIRATORY DISORDERS

CROSS-REFERENCES TO RELATED APPLICATIONS

The present application is a continuation-in-part application of application Ser. No. 09/908,176, dated Jul. 19, 2001, for METHOD AND DEVICE FOR ORGANIZING AND COORDINATING THE COMBINED USE OF LIQUID MEDICATIONS FOR CONTINUOUS NEBULIZATION FOR THE TREATMENT OF RESPIRATORY DISORDERS, in the name of Robert E. Weinstein, now U.S. Pat. No. 6,571,790, which is a continuation-in-part application of application Ser. No. 09/325,486, dated Jun. 3, 1999, for A METHOD AND DEVICE FOR ORGANIZING AND COORDINATING THE COMBINED USE OF NEBULIZER SOLUTIONS FOR THE TREATMENT OF RESPIRATORY DISORDERS, in the name of Robert E. Weinstein, now abandoned, which is a continuation-in-part application of application Ser. No. 08/855,893, dated May 12, 1997, for METHOD AND DEVICE FOR ORGANIZING AND COORDINATING THE COMBINED USE OF TOPICAL AEROSOLS FOR THE TREATMENT OF DISORDERS, in the names of Robert E. Weinstein and Alan M. Weinstein, now U.S. Pat. No. 5,941,241.

STATEMENT REGARDING FEDERALLY SPONSORED RESEARCH OR DEVELOPMENT

Not Applicable

REFERENCE TO A SEQUENCE LISTING, A TABLE, OR A COMPUTER PROGRAM LISTING COMPACT DISK APPENDIX

Not Applicable

BACKGROUND OF THE INVENTION

1. Field of the Invention

The present invention relates to a method and device for organizing, storing, and coordinating the combined use of liquid medications for continuous inhalation which are delivered by a nebulizer device for the treatment of respiratory tract disorders for the purposes of simplification, convenience, reducing medication error and increasing therapeutic compliance.

2. Description of the Related Art

Many drugs are utilized by patients over a period of time in varying amounts and in varying order to provide for their effective administration. Packaging has been developed for aiding the user of such drugs to comply with their proper administration over the proper time period. The dispensing apparatus associated with such multiple-day administrative drugs are typically directed to the administration of pills, capsules, or similar solid medication.

U.S. Pat. No. 4,039,080, for example, discloses a tray having individual compartments for pills which may contain a week's medication with indicia indicating the day of the week and time of the day the medication is to be taken. U.S. Pat. No. 4,553,670 discloses another device comprising a support on which are located two different ingestible medicinal substances in a single-dose form with an adjacent portion for instructional information. U.S. Pat. No. 4,593,819 discloses a covered pill tray of rectangular configuration having an array of open-topped compartments to hold a supply of medication arranged by the day and time of taking the medication. U.S. Pat. No. 4,736,849 discloses a method and another type of dispenser for the storage and dispensing of calendar-oriented pills. U.S. Pat. No. 5,181,189 discloses a device for storage and time-regulated dispensing of drugs which includes a drug container to which is secured a signal generator. U.S. Pat. No. 5,377,841 discloses a sleep therapy package which includes an audio recording of program material for inducing sleep, a card having a plurality of doses, some of which are medicine for inducing sleep and at least one of which is placebo, along with patient instructions. U.S. Pat. No. 5,830,490, discloses a method and device for organizing and coordinating topical aerosols together with oral medications for treating respiratory disorders.

While the marketplace abounds with pill boxes and organizers for oral medications, and while a device to organize multi-dosage aerosol units and oral medications has been disclosed, no organizational tool is presently available for a lay person to organize medications which are provided to the user in liquid form for administration by continuous nebulization.

Because the respiratory tract is structured as a conduit for air, it is possible to deliver medication to the respiratory tract topically by aerosol to treat respiratory tract disorders. This may be accomplished with hand-held metered dose devices that deliver a single bolus of aerosol. The aerosol can be derived from liquid medication released from a pressurized canister (for example, Serevent® Inhalational Aerosol), or solid powdered medication particles which are dispersed in a chamber and deliberately inhaled (for example, Serevent Discus®). Alternatively, medication can be delivered to the respiratory tract by continuous nebulization of a liquid medication by a venturi type nebulizer or ultrasonic nebulizer as are well-known in the art. Continuous nebulization, typically over a period of minutes, is preferred, particularly for individuals who are unable to coordinate their inhalational effort or who are otherwise unable to master the technique of using hand-held metered dose inhalers, for example, infants, young children, and debilitated individuals. If continuous nebulization is desired, the user is required to employ a nebulizable medicinal liquid supplied in its own container and dispense the prescribed amount of the medication into the nebulization device for nebulization. Such containers are non-pressurized so as to allow them to be opened by a user and thereby convey the contents to the nebulization device. This is in contrast to the pressurized containers of metered dose inhalers that are often employed for treating respiratory disorders. The medicinal liquids for continuous nebulization are obligatorily packaged in non-pressurized containers. Examples of such non-pressurized containers include single-dose vials or a multiple-dose bottle with calibrated dropper.

Examples of such medicinal nebulizer liquids currently employed for continuous nebulization treatment of respiratory disorders include: Ventolin Nebules® marketed by Glaxo-Wellcome consisting of an inhalational solution of albuterol sulfate, 0.083% and packaged as 2.5 mg in a 3 ml plastic vial with a twist-off top, Proventil albuterol sulfate inhalational solution marketed by Schering consisting of albuterol 0.5% and supplied in a 20 ml amber bottle with a calibrated dropper, cromolyn sodium inhalational solution, USP marketed by Dey consisting of 20 mg of cromolyn sodium per 2 ml and packaged in a 2 ml plastic vial with a twist-off top, Atrovent® ipratropium bromide inhalational solution, 0.02% marketed by Boehringer Ingelheim and packaged in a 2.5 ml plastic vial with a twist-off top, Mucosil™ acetyl cysteine 10% and 20% solutions marketed by Dey in 4 to 100 ml vials, metaproterenol sulfate inhalation 0.4% and 0.6% solutions marketed by Dey as 2.5 mL vials, Alupent® metaproterenol 5% inhalational solutions marketed by Boehringer Ingelheim and in 10 and 30 ml bottles with a calibrated dropper, Xopenex™ Inhalation Solution consisting of 0.63 or 1.25 mg of lavalbuterol HCl in a single-dose, low density polyethylene vial, and marketed by Sepracor, sterile water for inhalation, USP, and sodium chloride inhalation solution, USP in concentrations ranging from 0.45% to 10% provided in 3 to 15 ml vials by Dey. This is not meant to be an exhaustive list and it is anticipated that additional liquid medications for continuous nebulization will come to the marketplace.

The term "liquid" as used in the present specification is meant to relate to its ordinary dictionary meaning which pertains to a material having a flowing or fluid quality, and to relate to medicinal agents in the form of solutions, mixtures, suspensions, and the like which, at the time of use, are fluid in nature, can be transferred by pouring or flowing into a continuous nebulizer apparatus, and can be continuously nebulized. The aforementioned examples of these liquids also relate to particular containers which may be used to contain the liquid agents in a manner such that they may be dispensed by the user into a continuous nebulizer apparatus. The phrase "vial with a twist-off top" is meant to denote a single-dose container containing liquid and which is opened by twisting, tearing, snapping, or otherwise mechanically removing a portion of the container wall to expose its contents, which can then be poured into a nebulizer apparatus. Such single-dose containers are well known in the art and may be referred to in common usage as vials, pouches, bottles, or by a trade name. Such containers are typically uniform in material, contain the medicinal liquid within a bubble in the material, and are formed with a weakened, thin, or scored area in the wall of the bubble where they may be opened.

The term "bottle with a calibrated dropper" refers to a bottle which is larger than a single-dose vial, typically of plastic or glass, and which can contain multiple doses of liquid medications for nebulization. Such bottles can be re-closed. A calibrated dropper allows the user to dispense the liquid to be nebulized into a continuous nebulizer apparatus.

Liquid medications for continuous nebulization may be used alone, but it is often desired to use them in combination. It is recognized that continuous nebulization is typically utilized by infants, young children, and debilitated individuals because of the inability of such individuals to coordinate their inhalational effort or are otherwise unable to master the technique of using hand-held metered dose inhalers. It is not uncommon for a young mother to be required to administer continuous inhalation treatments to an infant or young child suffering from a respiratory disease, such as asthma, many times per day, and such treatments are typically required over periods of months to years. Each treatment may consist of a multiplicity of agents and the agents may be required to be given separately or mixed together. The order of administration may be important, for example, administering a fast-acting bronchodilator to open the airways before administering other agents, so as to allow better penetration of the subsequent agent(s). In some instances, the same combinations of medication may be given at each treatment time, and in others, the medications at each treatment time may vary, for example, different agents for morning and evening.

Multiple and variously packaged medicinal continuous nebulization liquids may be prescribed for use in conjunction with each other to comprise a treatment regimen for respiratory diseases. In the current state of the art, each agent is separately packaged, separately prescribed, and separately instructed. It is noteworthy that the amount of each liquid and frequency of use may vary with each medication. An important consideration of the present invention is that the medications, as they are presently dispensed, contain neither teaching nor instruction to coordinate the use of one agent with another, although such medications are often used together as a regimen. Moreover, in some instances it is required to employ a diluent to properly prepare a concentrated solution for nebulization, particularly in the case of medications that are packaged in multidose bottles, such as albuterol 0.5%. It is perceived that the present requirement for separately prescribed, separately acquired, and separately instructed continuous nebulization medications introduces a significant source of inconvenience, disorganization, potential for confusion and error for a particularly vulnerable sector of caregivers and recipients, which the present invention seeks to remedy.

The asthma death rate has notably increased in the United States in recent years, in part attributable to lack of patient compliance with multiple medications regimens. There is clearly a need for a method of reducing medication error and for enhancing therapeutic compliance with continuously nebulized topical respiratory regimens.

It is well known that simplicity and ease of use benefit medication compliance, and effective therapy. A device to organize, simplify, and thereby enhance ease of use and compliance with multiple liquid medications for continuous nebulization, has been overlooked. No pharmaceutically formulated device that combines such nebulization liquids together into a single organized package regimen with clear indicia and coordinated instruction is presently commercially marketed or available to a user. It is therefore the object of the present invention to provide these devices and methods.

BRIEF SUMMARY OF THE INVENTION

In accordance with the foregoing objectives, the present invention comprises a device for reducing medication error and enhancing therapeutic compliance with the combined use of inhalational solutions for treating respiratory disorders such as bronchitis, emphysema, asthma, cystic fibrosis, and bronciectasis, comprising: (a) at least two liquid medications for continuous nebulization to the respiratory tract in separate non-pressurized containers; (b) indicia for distinguishing the liquids; (c) instructions for coordinating use of the liquids together; and (d) a unifying container. The present invention may optionally include an apparatus for measuring outcomes of using the nebulized liquids. The present invention further comprises a method to enhance convenience, reduce medication error and enhance compliance with combined liquid medications for continuous nebulization for treatment of respiratory tract disorders.

BRIEF DESCRIPTION OF THE DRAWINGS

For a fuller understanding of the nature and object of the present invention, reference is made to the accompanying drawings, wherein.

DETAILED DESCRIPTION OF THE INVENTION

Figure 1:
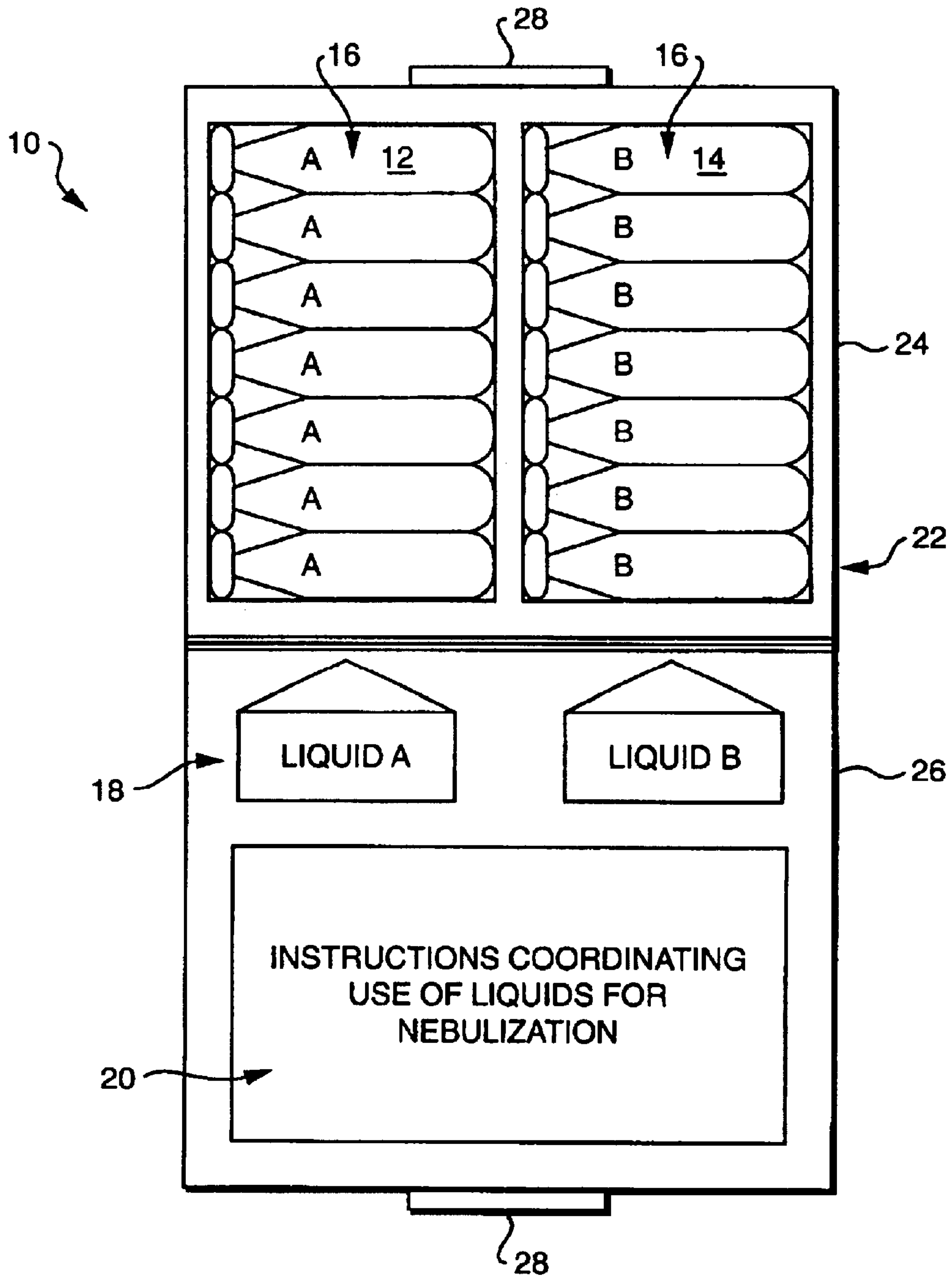
FIG. 1 is a plan view of a container containing two different inhalational solutions in single-dose vials in accordance with the present invention.

The following detailed description of the invention is provided to aid those skilled in the art in practicing the present invention. However, it should not be construed to unduly limit the present invention. Variations and modifications in the disclosed embodiments may be made without departing from the scope of the present inventive discovery.

The present invention provides a unifying dispensing container for medicaments for treatment of disorders requiring combined use of liquids intended to be continuously nebulized and a method for reducing medication error and enhancing therapeutic compliance of combined continuously nebulized inhalational liquids for treatment of such disorders. The unifying container holds at least two liquids for nebulization, each in its own non-pressurized container, indicia for distinguishing these liquids and instructions for their use together as a single therapeutic regimen. Apparatus to measure outcomes of using the nebulized liquids may also be included. It is to be understood that the word, "nebulize," in the context of this application refers to its ordinary dictionary meaning of reducing a liquid to a spray, which spray, in this instance, may then be directed to respiratory surfaces. It is to be understood that the word, "non-pressurized," refers to the pressure within the container being not substantially greater than sea level atmospheric pressure, in contrast to the elevated pressure utilized by aerosol producing containers such as those used in metered dose inhalers.

Referring to the drawings, it will be understood that while preferred embodiments of the invention have been illustrated and described, the invention is not limited to such embodiments. For example, the present invention contemplates the employment of any non-pressurized container that can be adapted for this use. Changes and additions may be made therein and thereto without departing from the spirit of the invention.

Figure 3:
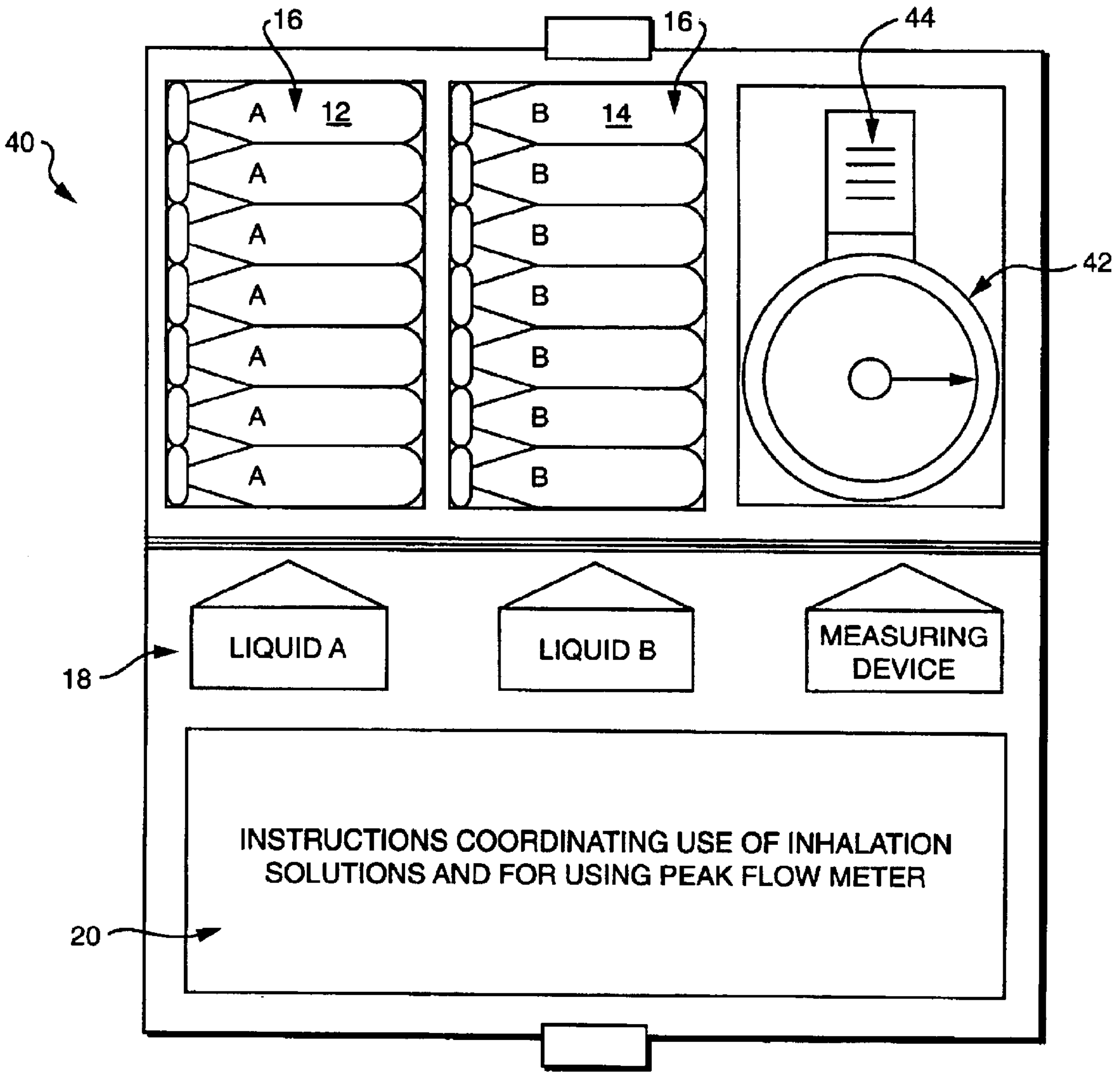
FIG. 3 is a plan view of a container in accordance with the present invention incorporating a peak flow meter to measure the outcome of utilizing the nebulized medication and where the instructions include directions for the proper use of the measuring device.
Figure 4:
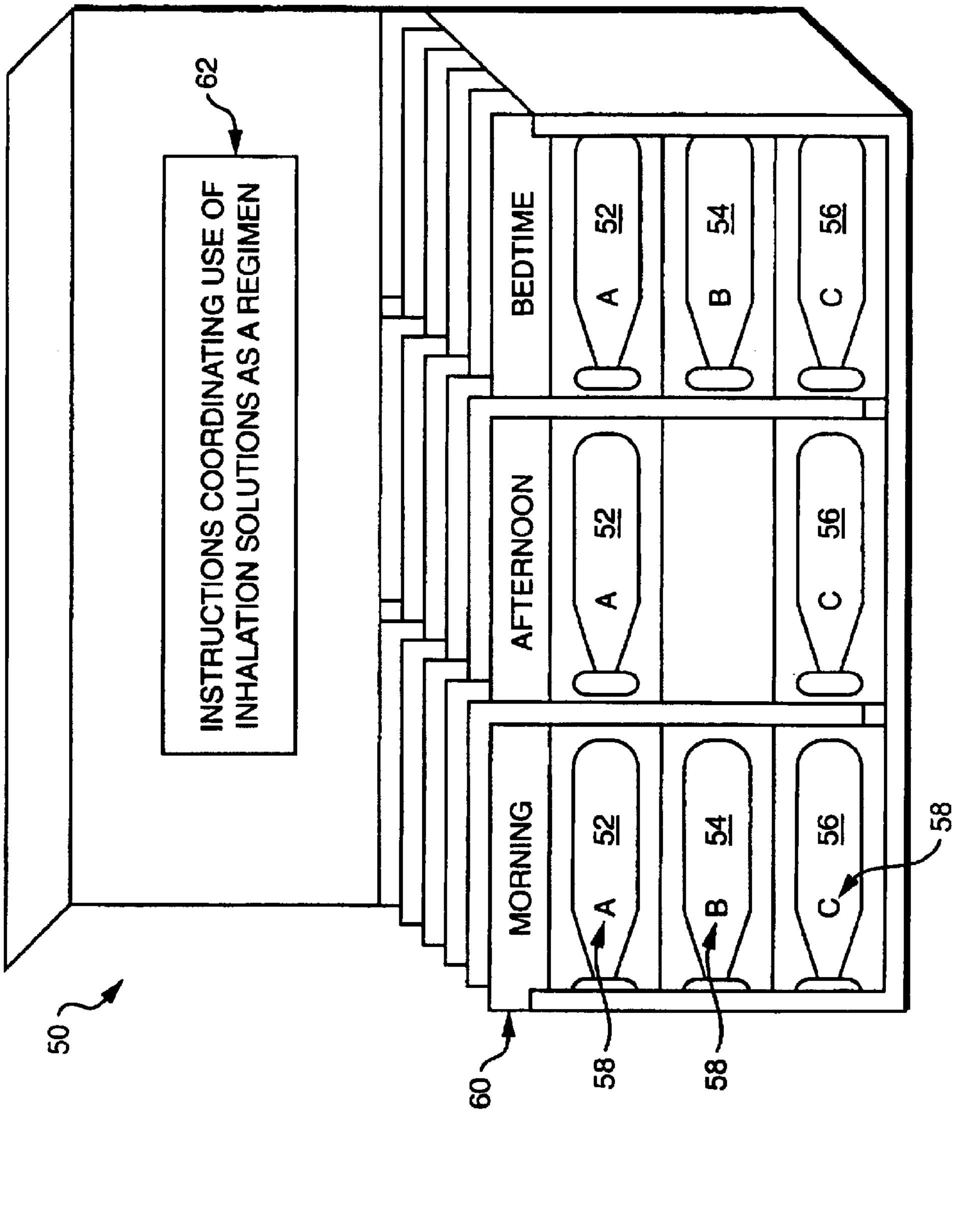
FIG. 4 is a perspective view of a container containing a regimen of more than two different liquid medications for continuous nebulization in accordance with the present invention, the liquids arranged according to time of day of recommended use.
Figure 5:
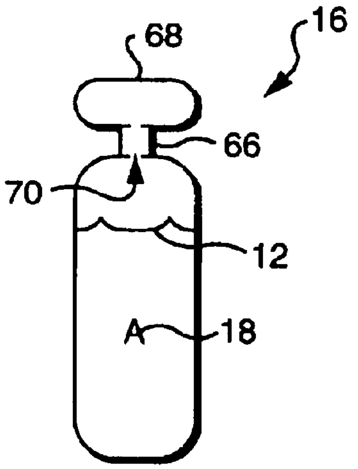
FIG. 5 is a detailed view of the single-dose vial of FIG. 1.

Four embodiments of the unifying container of the present invention are respectively depicted in FIGS. 1–4. In FIG. 1, a support package 10 which has structure for housing, and which houses two different liquids for continuous nebulization 12, 14, each in its own single dosage vial 16, is illustrated. The single-dose vial 16, shown in FIG. 5, is well-known in the art. It is a small, typically plastic, container with a neck 66 and a top 68. The top 68 is twisted until it breaks off at the neck 66, revealing an opening 70 through which the liquid 12 can be poured. The term "top" is herein used to denote the area of the container which, when breached, allows egress of the liquid contents. Identifying indicia 18 that distinguish the liquids is provided both on the support container and on the vials. Instructions 20 for the use of the liquids 12, 14 together as a regimen is provided on the support container 22. Such instructions 20 are in accordance with the medications used and the medicinal effects desired, and may instruct the use of both nebulized liquids together at the same time, or at differing times, or a combination together and alone a various times. Special circumstances for which each is best utilized may be instructed. The instructions 20 may be unalterable or may be capable of being altered yet maintained within the unifying container 22. The lid portion 26 and bottom portion 24 of the support package 10 each contain a respective clasp 28 which can be secured together when the support package 10 is folded along its fold.

Figure 2:
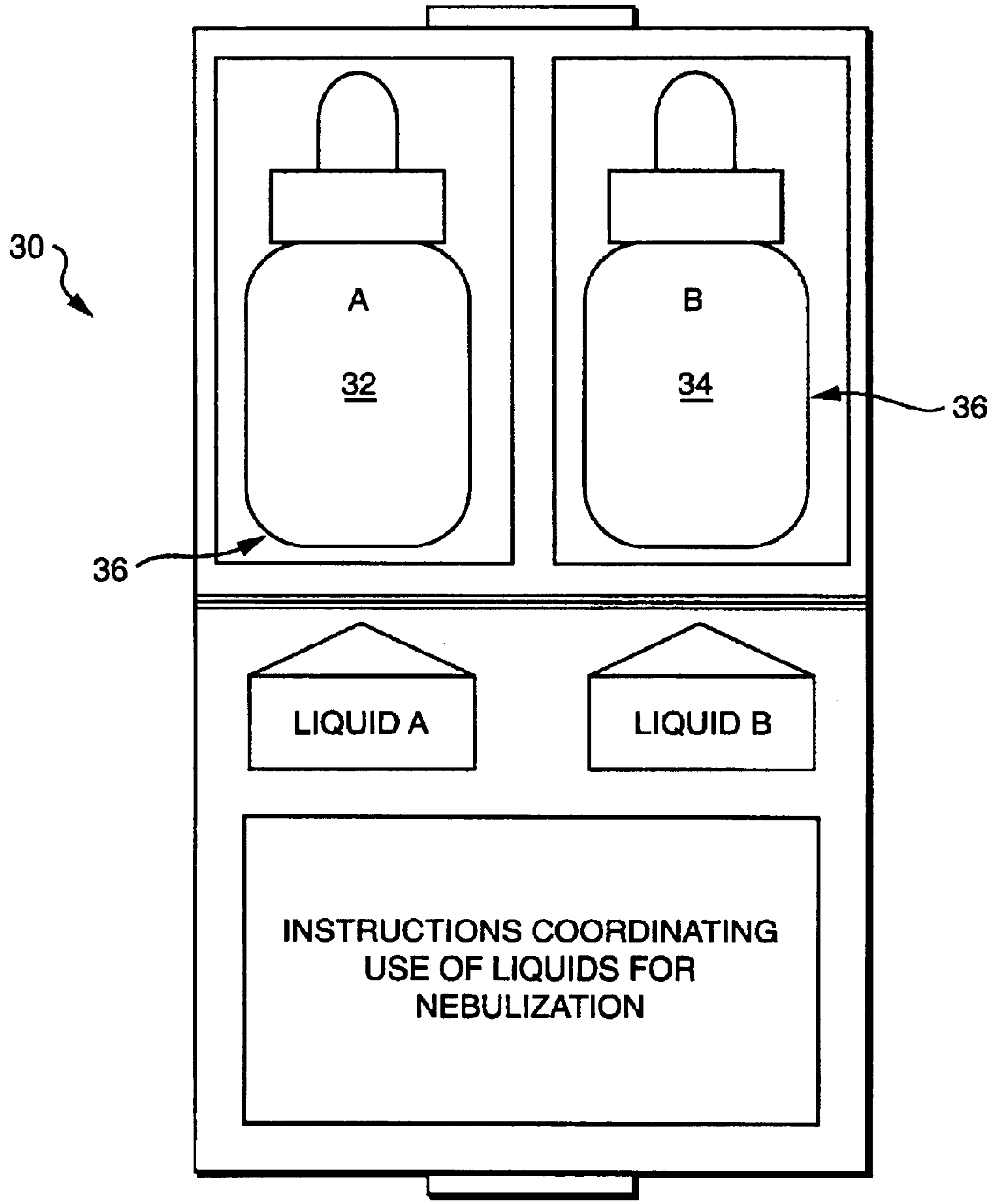
FIG. 2 is a plan view of another container containing two different inhalational solutions in multiple-dose bottles in accordance with the present invention.
Figure 6:
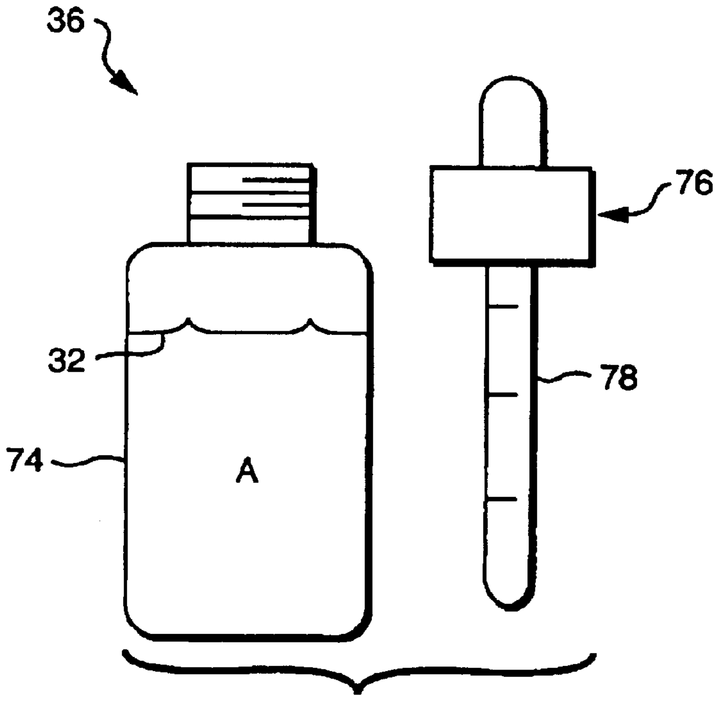
FIG. 6 is a detailed view of the multiple-dose bottle of FIG. 2.

FIG. 2 illustrates a support package 30 similar to that of FIG. 1 which contains two separate liquids 32, 34 for continuous nebulization, each in a multiple-dose bottle 36. The multiple-dose bottle 36, shown in FIG. 6, is well-known in the art. It is a glass or plastic bottle 74 with a screw cap 76 that includes a calibrated dropper 78. The dropper 78 may calibrated by dosage or by volume, such as milliliters (mls). FIG. 3 illustrates a support package 40 containing the elements of FIG. 1 and also incorporating a device 42 to measure the outcome of utilizing the medications. Simple devices for measuring outcomes, such as peak flow meters, are well known in the art. Instructions 44 for its use are contained in the measuring device, in this instance, by being included on its surface. FIG. 4 illustrates a support package 50 which contains three separate liquids for continuous nebulization 52, 54, 56 arranged according to a preferred regimen. In this instance, the positioning of the medications reflects their order of use. Distinguishing indicia 58 on the vials identify each liquid, and indicia 60 on the packaging indicate the use of all three medications for morning dosing, the first and third medications for the afternoon, and all three for bedtime. Instructions 62 on the packaging further teach and coordinate the use of the medications together as a regimen.

The packaging may be adapted in accordance with the requirements of the regimen by changing the configuration, the packaging, the housings, and indicia. Additionally, the packaging may be in any geometric configuration and the containers may be any suitable pharmaceutical container.

In the method of the present invention, the user dispenses the instructed amounts of the medications from their non-pressurized containers into a nebulization device for nebulization. The medications may be nebulized together or individually as desired for treatment.

Often it is advisable for individuals suffering from respiratory disorders such as bronchitis, emphysema, bronchiectasis, cystic fibrosis, or asthma to utilize a combination of nebulized medications as a treatment regimen. Treatments which necessitate a multiplicity of components pose a number of problems for patients. These multiple medication treatments may be a source of confusion and frustration which can result in medication error or lack of compliance.

Current treatments with a multiplicity of nebulized liquids lack coordinating indicia and instructions readily available to the patient which verify the multiple component use together. Patients are confronted with a multiplicity of medications and may lose track of which medication is which. Individual components, especially individual components purchased at separate times, may be lost, misplaced, or ignored, particularly so with instructions issued separately from the medication. Lacking organization, the least used, least immediate acting, or least obvious acting components, even if important or offering long-term effect, are the ones most likely to be lost or ignored.

Furthermore, in spite of careful oral and written instruction from the health care provider, many patients are known to use what they have conveniently available. These haphazard applications cannot only result in treatment failure, but also result in further expense for the patient who will ultimately have to seek additional consultation involving medical personnel time and expense to instruct and organize therapy for that individual. The devices and methods of the present invention will greatly help overcome these noted problems.

Additionally, cost factors, as well as outcomes, are now being carefully considered by medical care groups. There is a definite need for devices and methods that will help patients be more cognizant of their medications and therapy regimens. Such devices and methods will improve and ensure patient compliance. They will provide not only a means of further instruction but also provide an organizational tool which can save medical expenditures. Successful therapy is less costly than unsuccessful treatment.

Other embodiments of the present invention may include additional spirometric apparatus to measure treatment outcomes. An example of such apparatus is a peak expiratory flow meter. Other devices that measure parameters of airway patency are within the scope of this invention, as well as instructions for the use of the metering device and coordination of its use with the medication regimen. The incorporation of such a device would allow the patient to monitor his or her respiratory status, encourage compliance with the treatment regimen, and provide a warning of impending treatment failure in the case of lack of compliance. In the preferred embodiments, the inhalational liquids, the indicia, the spirometer, and the instructions are easily visible.

The choice of medications and their use together is dependent on numerous considerations besides mechanism of action and risks of the individual medications, and include absorption, time of onset after dosing, rate of elimination, duration of action after dosing, therapeutic effect by virtue of combination, and side effects by virtue of combination. Medication error and misuse due to a multiplicity of medications pose an additional risk. Medical/pharmaceutical expertise is clearly required to formulate and prepackage a treatment regime for a user utilizing a combination of liquid medications for continuous nebulization and formulate and prepackage appropriate instructions for use by a lay individual affected by respiratory disorders.

EXAMPLES

The invention will be further clarified by a consideration of the following examples, which are intended to be purely exemplary of the invention.

1. Example 1

One beneficial treatment regimen might consist of a selective beta-adrenergic bronchodilator and an anti-inflammatory agent. The regimen exemplified might be suitable for a moderately affected asthmatic whose symptoms are in good control. The anti-inflammatory agent, cromolyn sodium, is known to prevent asthmatic symptoms rather than reverse them, however success is generally contingent upon consistent usage over a period of time. The beta-adrenergic bronchodilator albuteral is known to have central nervous system side effects and dosage is limited and anticipatory of the times of day when asthma symptoms are most likely to occur: morning and night. Medications exemplifying this regime might be: Ventolin Nebules®, containing 2.5 mg of albuterol in 3 ml of solution, two times a day, and Intal® Nebulizer Solution, one ampoule containing 20 mg of cromolyn sodium in 2 ml of purified water, three times a day.

2. Example 2

Another treatment regimen might include the anticholinergic agent ipratropium to reduce secretions, together with the medications of Example 1. This regime would then be comprised of Ventolin Nebules®, one nebule two times a day, Intal® Nebulizer Solution, one ampoule three times a day, and Atrovent® Inhalation Solution, which contains ipratropium bromide 500 mcg in 2.5 ml normal saline, three times a day. This regimen might be incorporated in the packaging of FIG. 4, where medication A represents Atrovent®, medication B represents Ventolin nebules®, and medication C represents Intal®.

3. Example 3

In the case of nebulizer solutions packaged in multiple-dose bottles, it is often required to use a second solution to properly prepare a solution for nebulization. The packaging of both solutions together is therefore considered. An example of such a package might include Proventil® Solution for Inhalation which contains albuterol 0.5% in a 20 ml amber glass bottle, and a second 120 ml bottle of sterile normal saline. Administration would typically consist of nebulization of 0.5 ml of albuterol and 3.0 ml of sterile normal saline together. This regimen might be incorporated in the package of FIG. 2, where medication A schematically represents Proventil® 0.5% solution and medication B represents sterile normal saline. The instructions would instruct in the proper mixing of the two for administration together each time they are used.

4. Example 4

Another regimen might include the use of a racemic albuteral together with ipratropium bromide to achieve selective adrenergic and anticholinergic therapeutic effects. This regime might then be comprised of Xopenex® Inhalation Solution which contains 0.63 mg of levalbuteral HCl and Atrovent® Inhalation Solution which contains 500 mcg of ipratropium bromide, each nebulized. This regimen might be incorporated in the package of FIG. 1, where medication A schematically represents Xopenex® and medication B represents Atrovent®, and the instructions teach the regimen of using both three times a day.

Other variations may occur to those skilled in the art which are within the scope of the invention as set forth in the appended claims. Those of skill in the art may recognize modifications to these presently disclosed embodiments. These variation and modifications are meant to be covered by the spirit and scope of the present claims.

I claim:

1. A prepackaged therapeutic device for reducing medication error and enhancing therapeutic compliance with combined use of liquid medications for continuous nebulization for the treatment of respiratory tract disorders, comprising:

(a) at least two liquid medications for continuous nebulization, said medications packaged in separate non-pressurized containers;

(b) indicia for distinguishing said liquid medications;

(c) instructions for coordination of said liquid medications use together as a single therapeutic regimen; and (d) a unifying container.

2. The device of claim 1 further comprising a spirometric device for measuring the effectiveness of using said medications.

3. The device of claim 2 wherein said device is a peak flow meter.

4. A method for reducing medication error and enhancing therapeutic compliance with combined use of liquid medications for continuous nebulization for the treatment of respiratory tract disorders, said method comprising the steps of:

(a) providing at least two liquid medications for continuous nebulization, said medications packaged in separate non-pressurized containers;

(b) providing indicia for distinguishing said medications;

(c) providing instructions for coordination of said medications use together as a single therapeutic regimen; and (d) providing a unifying container.

5. The method of claim 4 further providing a spirometric device for measuring the effectiveness of said liquid medications.

6. A method for reducing medication error and enhancing therapeutic compliance with combined use of liquid medications for continuous nebulization for the treatment of respiratory tract disorders, said method comprising the step of:

(a) providing a combined liquid nebulization regimen contained within a unified device, comprising (1) at least two inhalation solutions for continuous nebulization in separate non-pressurized containers, (2) indicia for distinguishing said liquid medications, (3) instructions for coordination of said liquid medications use together as a single therapeutic regimen, and (4) a unifying container;

(b) dispensing predetermined amounts of said liquid medications into at least one nebulization device according to said instructions; and (c) administering said liquid medications via said nebulization device according to said instructions.

7. The method of claim 6 further providing a spirometric device for measuring the effectiveness of said liquid medications.

* * * * *